(12) United States Patent
Siccardi et al.

(10) Patent No.: US 8,579,904 B2
(45) Date of Patent: Nov. 12, 2013

(54) INSTRUMENT FOR POSITIONING AN INTERVERTEBRAL IMPLANT FOR THE FUSION BETWEEN TWO VERTEBRAL BODIES OF A VERTEBRAL COLUMN

(75) Inventors: Francesco Siccardi, Vico Morcote (CH); Meinrad Fiechter, Lugano (CH); Dezső Jeszenszky, Küsnacht (CH); Zsolt Fekete, Bremen (DE); Christoph E. Heyde, Leipzig (DE)

(73) Assignee: Medacta International SA, Castel San Pietro (CH)

( * ) Notice: Subject to any disclaimer, the term of this patent is extended or adjusted under 35 U.S.C. 154(b) by 17 days.

(21) Appl. No.: 13/458,152

(22) Filed: Apr. 27, 2012

(65) Prior Publication Data

US 2012/0277810 A1    Nov. 1, 2012

(30) Foreign Application Priority Data

Apr. 29, 2011    (EP) ..................................... 11164259

(51) Int. Cl.
*A61B 17/70*    (2006.01)

(52) U.S. Cl.
USPC ....................................... 606/86 A

(58) Field of Classification Search
USPC ................ 606/246, 279, 86 A, 99; 623/17.11–17.16; D08/72
See application file for complete search history.

(56) References Cited

U.S. PATENT DOCUMENTS

| | | | |
|---|---|---|---|
| 6,066,174 A * | 5/2000 | Farris | 606/206 |
| 6,159,215 A * | 12/2000 | Urbahns et al. | 606/86 R |
| 6,319,257 B1 | 11/2001 | Carignan et al. | |
| 6,923,814 B1 | 8/2005 | Hildebrand et al. | |
| 2004/0153065 A1 * | 8/2004 | Lim | 606/53 |
| 2005/0096745 A1 * | 5/2005 | Andre et al. | 623/17.11 |
| 2006/0235426 A1 * | 10/2006 | Lim et al. | 606/99 |
| 2008/0287957 A1 | 11/2008 | Hester et al. | |
| 2008/0306488 A1 | 12/2008 | Altarac et al. | |
| 2009/0112217 A1 | 4/2009 | Hester | |
| 2009/0254182 A1 | 10/2009 | Kovarik et al. | |
| 2009/0276049 A1 * | 11/2009 | Weiland | 623/17.16 |

FOREIGN PATENT DOCUMENTS

| | | | |
|---|---|---|---|
| EP | 1841385 B1 * | 3/2010 | |
| FR | 2717068 A1 | 9/1995 | |
| WO | 03037228 A2 | 5/2003 | |
| WO | 2008146983 A1 | 12/2008 | |
| WO | 2010045301 A1 | 4/2010 | |

\* cited by examiner

*Primary Examiner* — Pedro Philogene
*Assistant Examiner* — David Comstock
(74) *Attorney, Agent, or Firm* — Allen, Dyer, Doppelt, Milbrath & Gilchrist, P.A.

(57) ABSTRACT

An instrument positions an intervertebral implant for the fusion between two vertebral bodies of a vertebral column. The instrument may include a handle having a proximal and a distal end, a locking shaft extended from the distal end of the handle, and a grasping head at the distal end of the shaft. The locking shaft may be cannulated, and a stem may be hosted inside the cannulated shaft passing through the handle. The stem may be free to rotate with respect to the locking shaft, or vice versa, while the grasping head may be formed at the distal end of the stem with a couple of prongs or clamps toward the other according to an angular relative rotation of the stem with respect to the locking shaft. The instrument may allow the surgeon to grip a corresponding implant with a simple rotation movement of his hand.

11 Claims, 16 Drawing Sheets

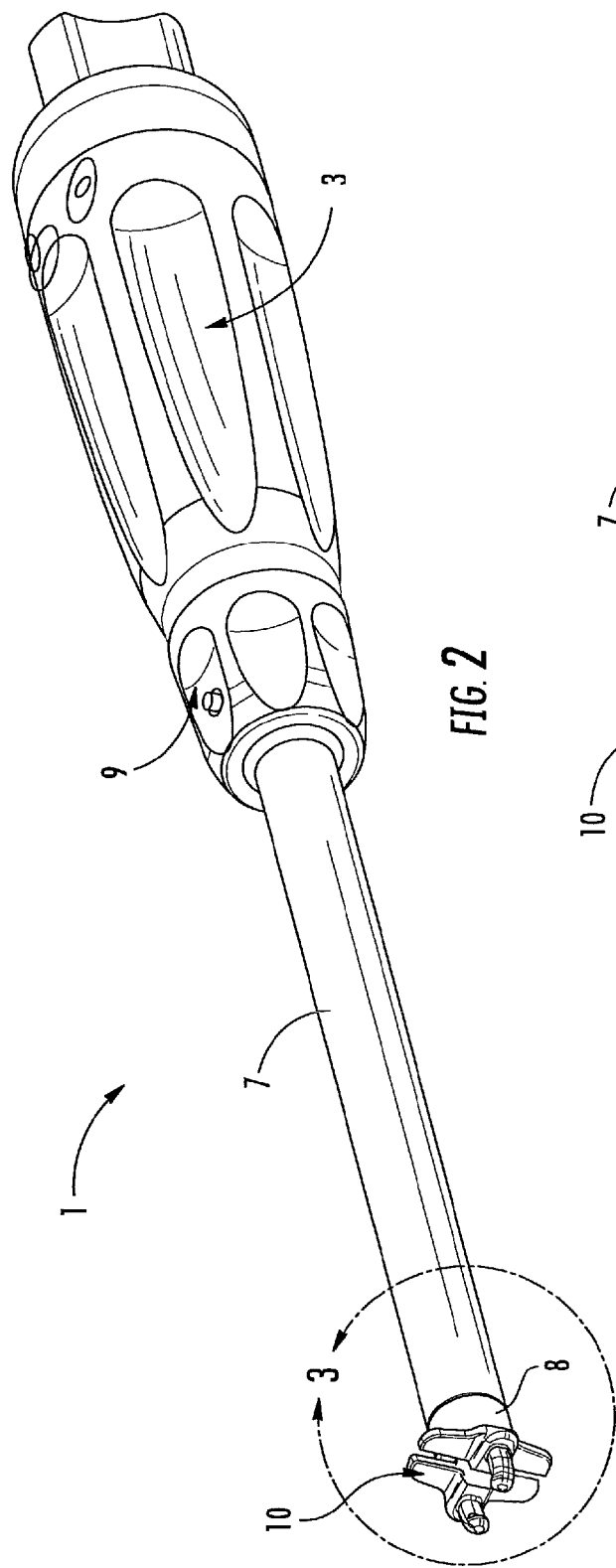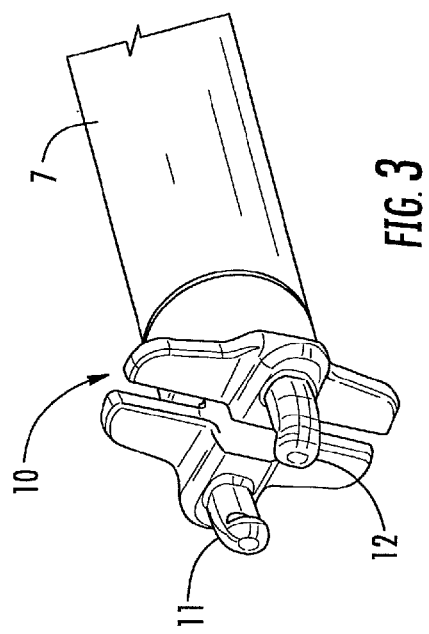

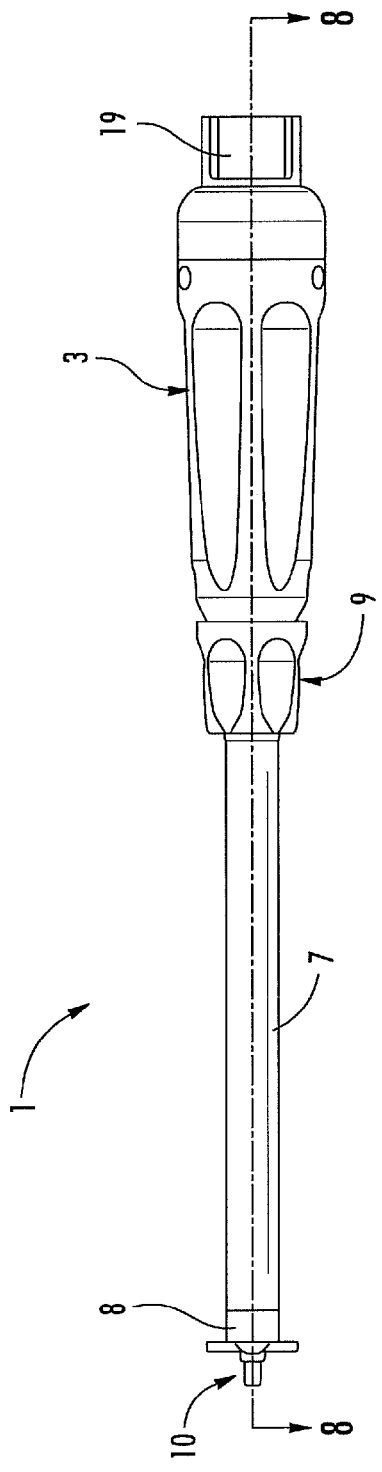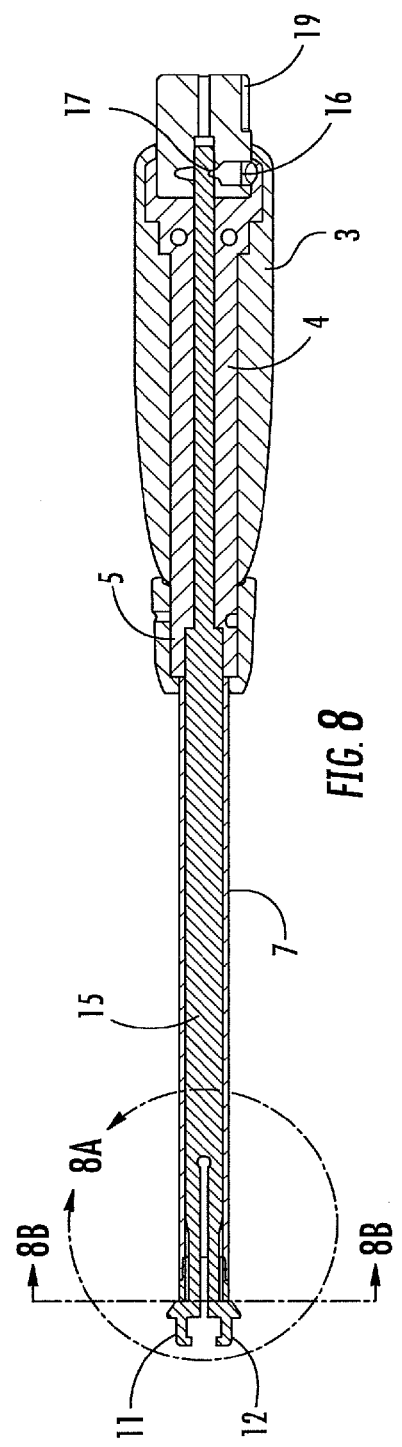
FIG. 7
FIG. 8

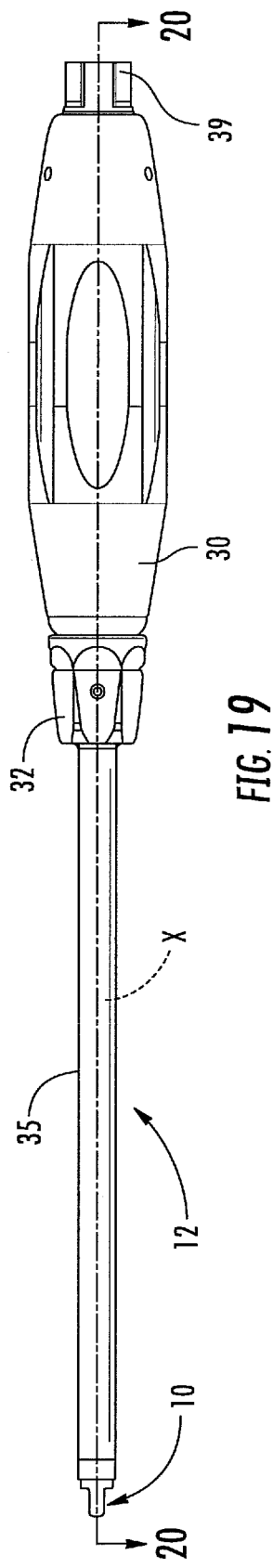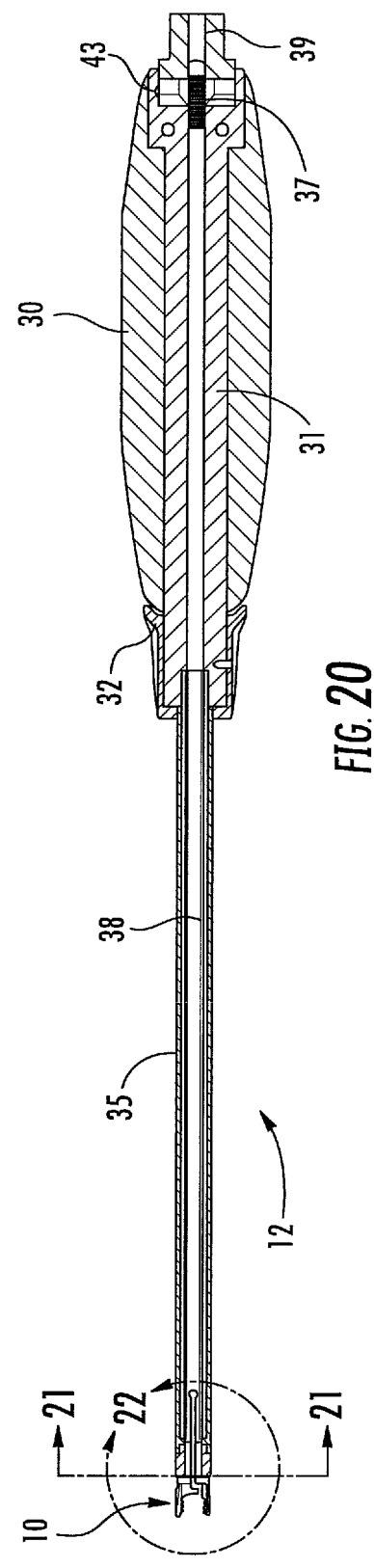
FIG. 19
FIG. 20

INSTRUMENT FOR POSITIONING AN INTERVERTEBRAL IMPLANT FOR THE FUSION BETWEEN TWO VERTEBRAL BODIES OF A VERTEBRAL COLUMN

FIELD OF THE INVENTION

The present invention relates to an instrument for positioning an intervertebral implant for fusion between vertebral bodies of a vertebral column.

BACKGROUND OF THE INVENTION

A known approach is disclosed in U.S. Pat. No. 6,159,215, which discloses a method for delivering a vertebral body spacer to the disc space. The instrument has two fingers, which are movable relative to one another and adapted to grip the spacer when the shaft is moved to actuate the fingers. The handle portion includes a grip and a trigger toward the grip for causing the fingers to move toward one another. The fixation is done by way of an extensive linear movement.

Another approach is described in U.S. Patent Application Publication No. 2006/0235426, which discloses an implant, an instrument, and a method for positioning a spinal implant in a spinal disc space between adjacent vertebrae. That implant is fixed by a hinged forceps tip. The forceps tip can be angularly adjusted with respect to the implant, and the instrument is permanently connected to the implant. This approach has a complex instrument locking mechanism instead of a 90° lock/unlock mechanism and it may be impossible to engage the instrument in-situ.

Another approach is disclosed in U.S. Pat. No. 6,066,174, which discloses an implant insertion device including a gripping device on one end. The jaws are movable between the grip position to grasp the implant between the gripping elements and release position to release the implant. A hollow sleeve is slideably disposed over the jaws for forcing the jaws together towards the gripping position. The implant fixation is done with a linear movement of the sleeve, but this linear movement can cause tissue damage and it is not as simple as a 90° locking.

Another approach is described in U.S. Patent Application Publication No. 2004/0153065. The approach is related to an intervertebral implant. The instrument is connected to the implant by a hinge element. The rotation of the axial sleeve of the instrument case is an axial movement of the shaft. This movement is pivoting about the spacer. It may be difficult to engage the instrument is-situ. Angulation is mainly possible in only one direction. The engagement/disengagement mechanism may be complex and uncomfortable.

Another approach is U.S. Patent Application Publication No. 2005/0096745, which discloses an implant for the transforaminal intercorporal fusion of lumbar vertebral column segments. The attachment part to the instrument is configured as a slot. Within this slot, the instrument can be engaged. The instrument can be fixed in different angles with respect to the implant. The interface is a friction lock, which has inferior stability compared to a positive lock. The fixation is done by a thread mechanism. The engagement/disengagement mechanism is less desirable than a 90° locking mechanism because of the used working steps.

Another approach is disclosed in European Patent No. EP1841385B1, which discloses an implant for the transforaminal intercorporal fusion of lumbar vertebral column segments. The attachment part to the instrument is configured as a revolute joint. Within the revolute joint, there is a threading as an interface to the instrument. The instrument can be fixed in different angles with respect to the implant. The interface is a friction lock, which may have reduced stability compared to a positive lock. In addition, in-situ engagement is not possible due to the threading. The fixation of the implant to the instrument is more difficult compared to a 90° locking instrument.

SUMMARY OF THE INVENTION

Based on the foregoing, it is an object of the invention to provide an instrument to be used for the transforaminal intervertebral fusion of lumbar segments of the vertebral column or anterior cervical discectomy and fusion or anterior lumbar intervertebral body fusion.

The instrument may allow a strong gripping action on the implant. Moreover, the instrument may have a simple structure and allow the surgeon to achieve the gripping of the corresponding implant with a simple movement of his hand.

More specifically, the present invention relates to an instrument for positioning an implant during a so-called lumbar interbody fusion (LIF) of segments of the vertebral column or a so-called anterior cervical discectomy and fusion (ACDF) of the cervical spine and the following description is focused on this specific technical field just with the purpose of simplifying its disclosure, since the instrument may also be used for other surgical operations of the spine.

Various attempts have been made to use minimally invasive surgery for spine operations. In this respect, so-called PLIF (Posterior Lateral Interbody Fusion) operation techniques have been developed. According to such an operation technique, the intervertebral disc is removed through a posterior access and an intervertebral space is filled with autologous bone.

Further developments of this PLIF technique resulted in the application of a so-called TLIF operation technique based on a transforaminal access. This technique provides for the dorsal transforaminal introduction of titanium cups (so-called cages), which are filled with autologous bone. At the same time, a dorsal instrumentation and stabilization is applied.

The advantage of the briefly outlined method may be that no transabdominal or retroperitoneal additional access has to be used. However, the instrument can also be used for an Anterior Lumbar Interbody Fusion (ALIF) where a transabdominal or retroperitoneal access is used.

An aspect is directed to an instrument for gripping and positioning an intervertebral implant having an handle, a locking shaft, a grasping head having a couple of prongs or clamps for grasping the implant wherein the grasping head is driven in the opening and in the closing position by a simple relative rotation between the handle and the shaft.

According to this embodiment, the above technical problem may be addressed by an instrument for positioning an intervertebral implant for the fusion between two vertebral bodies of a vertebral column, comprising: a handle having a proximal end and a distal end; a locking shaft extended from the distal end of the handle; a grasping head at the distal end of the instrument; the locking shaft is cannulated and a stem is hosted inside the cannulated shaft and fixed to the handle; the locking shaft is free to rotate with respect to the stem; the grasping head being formed at the distal end of the stem with a couple of prongs or clamps coming close or far one toward the other according to an angular relative rotation of the locking shaft with respect to the stem.

The cannulated locking shaft has the distal portion having an internal oval section interfering with the stem during relative angular rotation. In this respect, a cut may be provided at the distal end of the stem, along its axis, thus separating the two prongs or clamps and allowing a reciprocal elastic movement between them.

A sleeve may be incorporated inside the handle with a distal end projection from the handle, the shaft being rotatable mounted on the distal end of the sleeve through a thumb wheel. The clamps of the grasping head may comprise internal teeth for improving the gripping action. The stem may be extended through the sleeve up to the proximal end of the handle and may have a threaded end to be fixed by a nut at the proximal end of the handle.

In another embodiment, the cannulated locking shaft may be rotatable with respect to the stem fixed to the handle. Nevertheless, it would be possible to provide an alternative construction with a stem rotatable with respect to a locking shaft fixed to the handle.

On the other side, a sleeve may be incorporated inside the handle with a distal end projecting from the handle; the shaft may be rotatable mounted on the distal end of the sleeve through a thumb wheel.

The stem may extend through the sleeve up to the proximal end of the handle and may have a threaded end to be fixed by a nut at the proximal end of the handle. In case the grasping head has clamps, they may comprise internal teeth for improving the gripping action. The locking action may be performed by rotational movement between 10° and 130°, either of the locking shaft or of the stem with respect to the handle.

Further features and advantages of the instrument of the present invention will appear from the following description given by way of non limiting example with reference to the enclosed drawings figures.

BRIEF DESCRIPTION OF THE DRAWINGS

FIG. 2 is a perspective view of an instrument realized according to the present invention for positioning an implant for the fusion between vertebral bodies of the spine;

FIG. 3 is an enlarged perspective view of the instrument of FIG. 2;

FIG. 7 is a side view of the instrument of FIG. 4;

FIG. 8 is a cross-sectional view of the instrument of FIG. 7;

FIG. 19 is a side view of the instrument of FIG. 15;

FIG. 20 is a cross-sectional view of the instrument of FIG. 19;

DETAILED DESCRIPTION OF THE PREFERRED EMBODIMENTS

Figure 1:
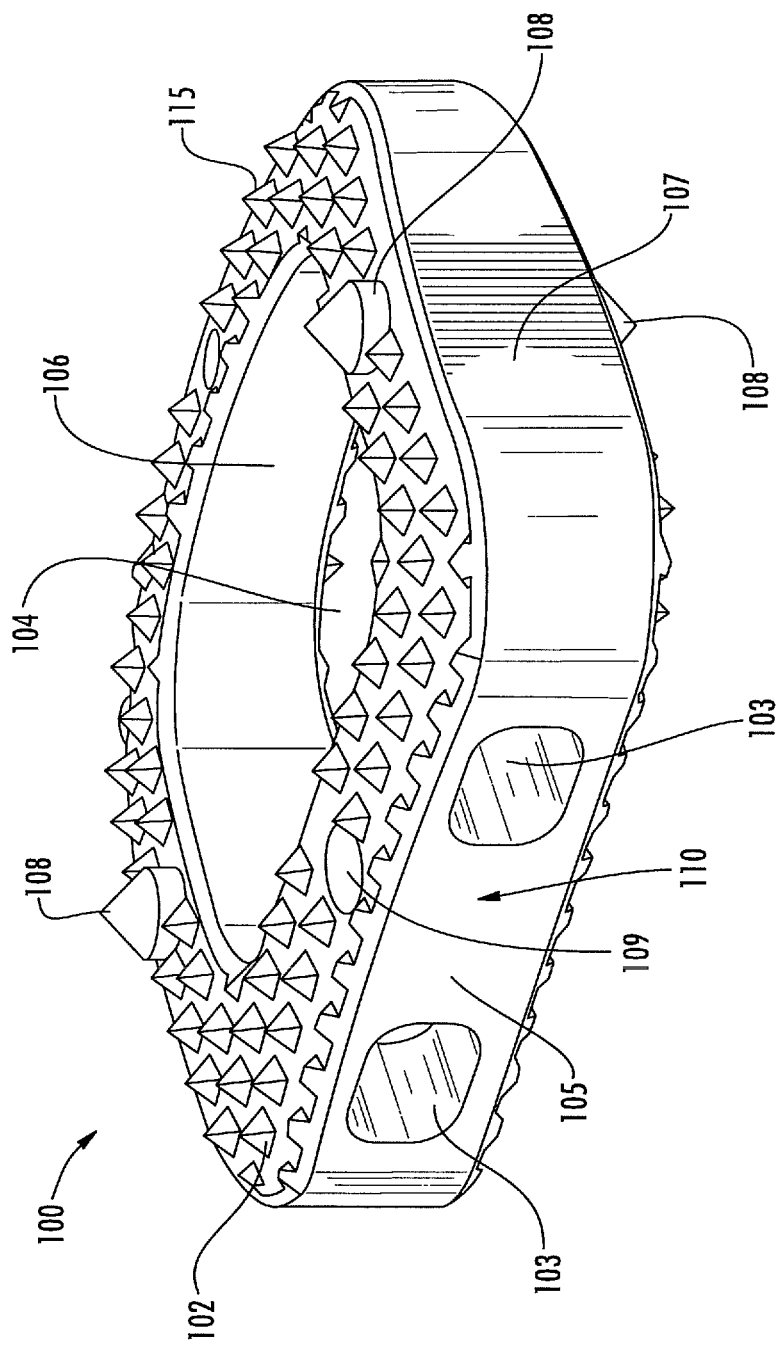
FIG. 1 is a perspective view of an implant for the fusion between two cervical vertebral bodies of a spine positioned by the instrument, according to the present invention.

With reference to the drawing figures, 100 is globally shown as an intervertebral implant to be positioned with the instrument 1 of the present invention for permitting the fusion between two vertebral bodies of a vertebral column. With reference to FIG. 1, the structure of the implant 100 is disclosed to allow a better understanding of its use and how the instrument 1 is suitable to grip such an implant 100 or other implants of similar use.

The implant 100 has been specifically realized for allowing vertebral operations according to the requirement of the modern Minimally Invasive Surgery. The implant 100 is mainly dedicated to the use in cervical intervertebral surgery, however, nothing prevents that it may be adopted in other surgery techniques, such as PLIF or ALIF.

The implant 100 has a main body 102 realized with a biocompatible radiolucent synthetic material, for example, a Polyetheretherketone (PEEK) structure having a favorable modulus of elasticity. The body 102 has substantially a ring shape squared with rounded edges and is available in several different heights, widths, and lengths.

As a whole, the body 102 has the form of a "D" having all rounded edges. There is a marker in each side of the implant body 102 to allow the surgeon to identify the implant when implanted. A typical marker 109 is provided in the opposite major sides 105, 106 while special markers 108 with sharpened ends are provided in each of the minor sides 107. All the inserted markers 108 or 109 may be manufactured by a suitable biocompatible alloy, for example, Titanium or a Titanium alloy.

The main purpose of the cone shaped projection of the markers 108 is to avoid post operative migration of the implanted implant. The major side 105 will be identified as a proximal major side since a portion of it will be gripped by the instrument 1.

The body 102 has two opposite surfaces coming into direct contact with the vertebral column in order to fit the anatomy of the vertebral end plates. Each of the surfaces includes a plurality of teeth 115 to provide primal stability and for improving the gripping or adhesion of these surfaces against the corresponding abutting surfaces of the vertebral end plates when the implant 100 is implanted.

The body 102 includes holes 103 or cavities 104 for filling purposes allowing the bone growth (e.g. autogenic bone graft). The portion of the proximal major side between the holes 103 is identified by the reference number 110. Advantageously, the holes 103 of the body 102 are used for receiving a gripping end 10 of the positioning instrument 1 realized according to the present embodiments.

In other words, the portion 110 of the proximal major side 105 between the holes 103 represents an engagement portion of the implant that may be gripped by the instrument head 10. The two holes 103 are passing through the thickness of the proximal major side 105 and have an internal tapered shape shown in the FIGS. 9 and 10.

Coming now to the examples of FIGS. 2 to 10, disclosed hereinafter in detail are the structure and functioning of an instrument 1 that may be used for handling the above-described implant 100 as well as for gripping other kind of implants. The instrument 1 is structured for positioning an intervertebral implant like the implant 100 in the spinal column, more particularly, in the cervical portion of the spine.

The instrument 1 allows grasping an implant like the implant 100 by the instrument grasping head 10 having a quick 90° oval locking feature. The connection between the grasping head 10 and the implant 100 is allowed by means of two prongs 11 and 12 of the grasping head 10 that are inserted into the corresponding holes 103 of the proximal portion 110 of the implant 100.

Different grasping mechanisms are described in the prior art but all those instruments need several turns to fix the implant to the instrument or a significant linear movement on the instrument or a complex hinge mechanism. A simple 90° rotation of the instrument thumb wheel provides a locking mechanism that significantly simplifies the engagement and disengagement of the implant 100 or of a similar implant structure, as detailed hereinafter.

In addition, typical instruments with a significant axial displacement can cause tissue damage. Pliers like instruments usually have an excessive space requirement, which is in such applications critical because it may require larger incisions and can usually not be used in Minimally Invasive Surgery.

The positioning instrument 1 for the cervical implant of the present invention comprises various components. A handle 3 that allows a secure holding of the instrument 1. Inside the handle 3, an elongated sleeve 4 is hosted and fixed. The distal end 5 of this sleeve 4 is cylindrical and on this distal end 5, it is mounted on a locking shaft 7 that is extended along an X axis aligned with the same axis of the handle 3. The locking shaft 7 terminates with a distal end including the grabbing head 10.

A collar 8 is mounted on the distal end of the locking shaft 7 while the grasping head 10 extends outside the collar 8. The locking shaft 7 is longer than the handle 3, and a movable connection between the shaft 7 and the distal end 5 of the sleeve 4 is obtained by a thumb wheel 9. This thumb wheel 9 is fixed to the proximal end of the shaft 7 while it is rotatably mounted on the distal end 5 of the sleeve 4.

Figure 5:
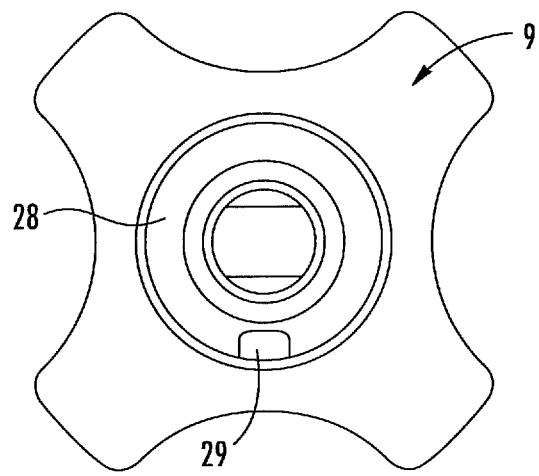
FIG. 5 is a front view of an instrument, according to the present invention.
Figure 6:
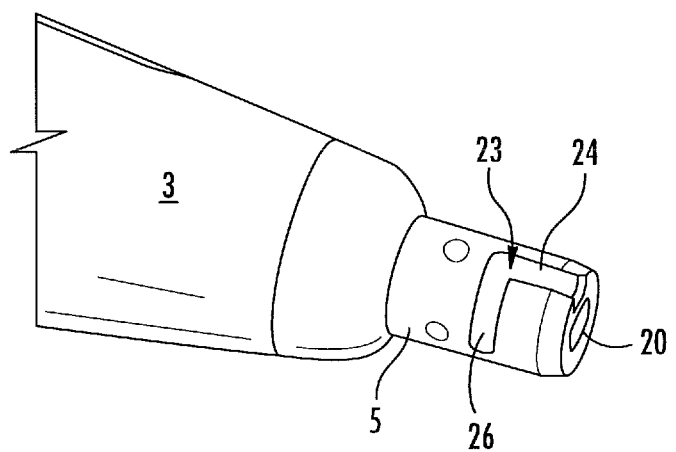
FIG. 6 is a perspective view of the instrument, according to the present invention.

The connection between the thumb wheel 9 and the distal end 5 of the sleeve 4 may be obtained in different manner but a bayonet coupling 13 may be preferred in this embodiment, as shown in FIGS. 5 and 6.

In more detail, the distal end 5 of the sleeve 4 includes a groove 23 having an L shape. A first portion 24 of this groove is elongated parallel to the axis X-X of the shaft 7, while a second portion 26 of this groove 23 is extended perpendicularly to the first groove portion 24 and for a predetermined angular extension that may vary from 10° to 130° according to the application needs.

A pin 29 is projected inside a cavity 28 of the thumb wheel 9. This pin 9 is inserted into the first groove portion 24 when the thumb wheel 9 is mounted on the distal end 5 of the sleeve 4. Then, the pin 29 is trapped into the second groove portion 26 of the L shaped groove 23 to allow an angular range of the thumb wheel 9 according to the length of the angular range of second groove portion 26.

The locking shaft 7 is cannulated and a stem 15 is inserted inside the shaft 7 and the sleeve 4 up to the proximal end of the handle 3. The longitudinal hole 21 forming the cannulated passage has an oval section only in correspondence of the tip or distal end, i.e. in correspondence of the collar 8.

Figure 4:
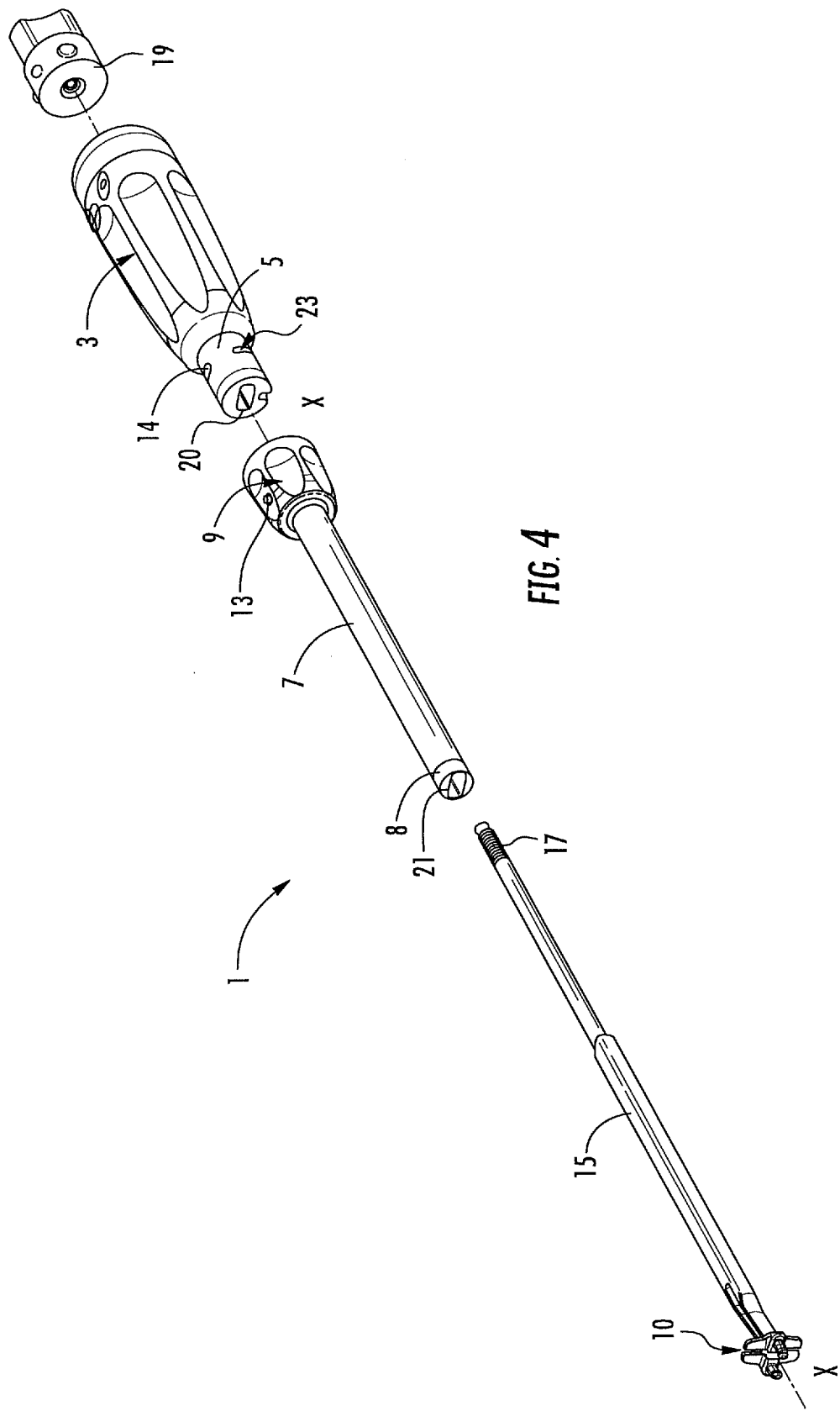
FIG. 4 is a perspective view of separate parts of the instrument of FIGS. 2 and 3.
Figure 8A:
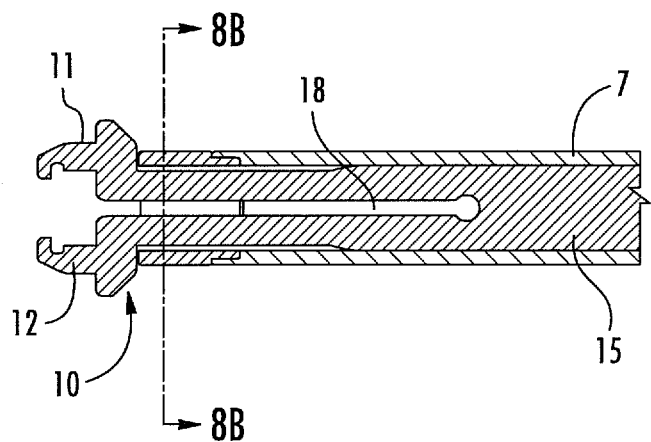
FIG. 8A is an enlarged cross-sectional view of FIG. 6 and in particular of the instrument distal portion.
Figure 8B:
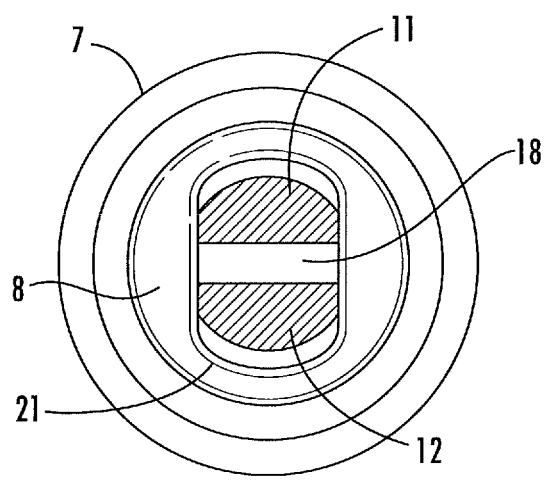
FIG. 8B is a cross-sectional view of the instrument distal portion taken along the line F-F of FIG. 7.

The remaining portion of the shaft 7 is cylindrical, as can be appreciated from the perspective view of FIG. 4, showing also the oval section 20 of the sleeve passage. As an alternative, the cannulated passage may have a rectangular section with rounded edges. The cross sections of FIGS. 8A and 8B show the shape of the stem 15 distal end and the internal oval section of the collar 8 at the distal end of the locking shaft 7, respectively.

In this embodiment, the stem 15 cannot be rotated with respect to the handle 3; the stem 15 is fixed with the handle 3.

It is only possible to rotate the locking shaft 7 with respect to the stem 15 and handle 3. The stem 15 may rotate just during the assembly phase to find the rectangular counterpart in the distal end 5 of sleeve 4.

The proximal end of this stem 15 is provided with a threaded portion 17 to allow the fastening of a terminal fastener nut 19, shown in FIG. 4. The nut 19 prevents the instrument from being disassembled when in use. A ball positioner 16 prevents the fastener nut 19 from falling out of the handle 3.

A person skilled in the art will appreciate that this relative movement may also be obtained in a different manner, thus leaving the shaft 7 fixed to the handle and allowing the stem 15 to rotate with respect to the shaft 7 and the handle 3. This possible alternative structure may be less readily handled but nothing prevents this approach in line with the principles of the present invention.

With reference to the examples of FIGS. 8A and 8B, it will now be disclosed the structure of the distal end portion of the instrument 1 of the present invention. The grasping head 10 is the distal terminal portion of the stem 15 and is formed by a couple of faced prongs 11, 12. Both prongs 11, 12 include a curved tip substantially corresponding to the internal tapered shape of the holes 103 of in the proximal major side of the implant 100.

Figure 12:
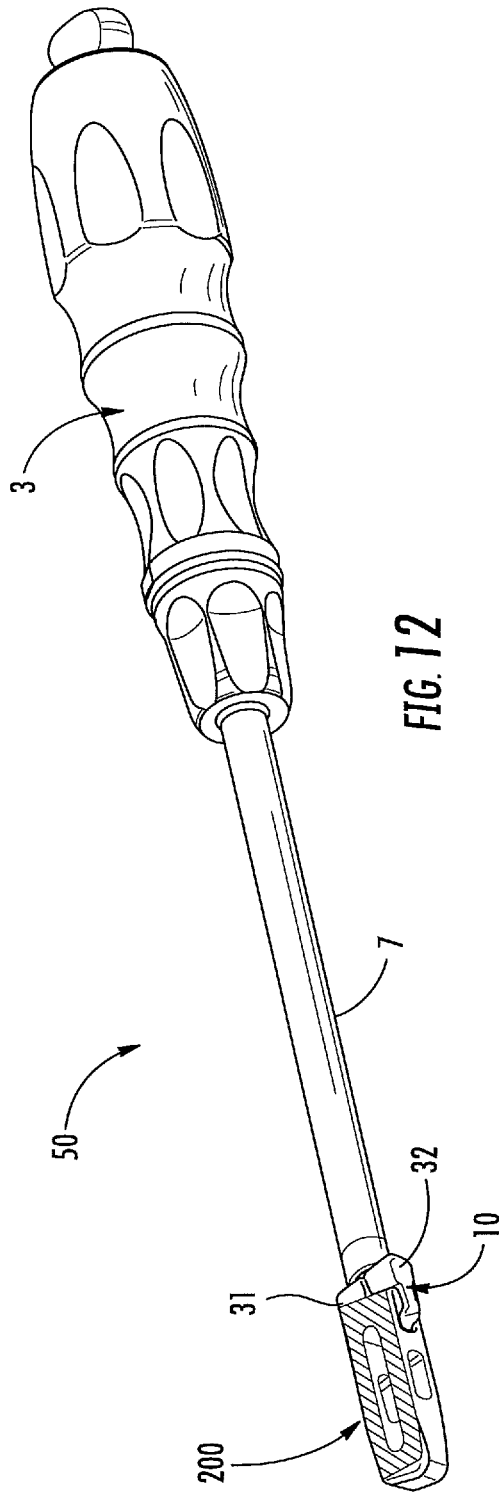
FIG. 12 is a perspective view of another embodiment of the instrument of the present invention.
Figure 13:
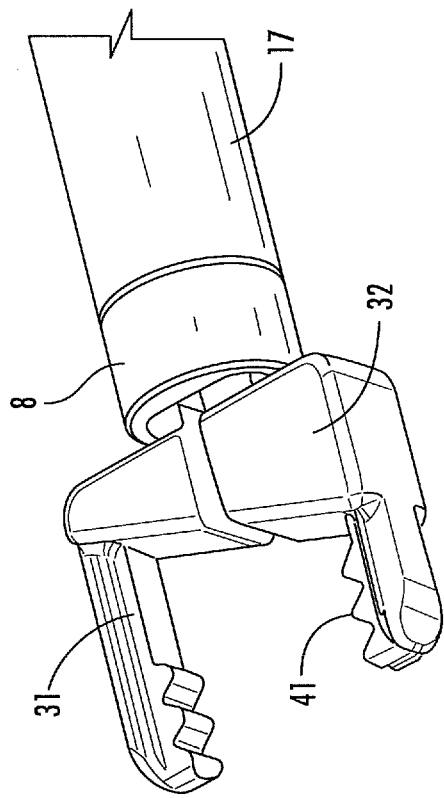
FIG. 13 is a perspective view of a part of the instrument of FIG. 12.

As an alternative, the grasping head 10 comprises faced clamps 31, 32, for example, as shown in FIGS. 12 and 13. These clamps 31, 32 are elastically movable getting closer or farther towards the other, substantially as the prongs 11, 12. A cut 18 is provided at the distal end of the stem 15 for a short extension along its axis thus separating the two prongs 11, 12 or the two clamps 31, 32 and allowing a reciprocal elastic movement between them. The extension of the cut is about 30%-40% longer than the extension of the oval section of the collar 8 to the shaft 7 distal end, as shown in FIG. 8A. The prongs 11, 12 or the clamps 31, 32 are formed integrally at the distal end of the stem 15.

Figure 9:
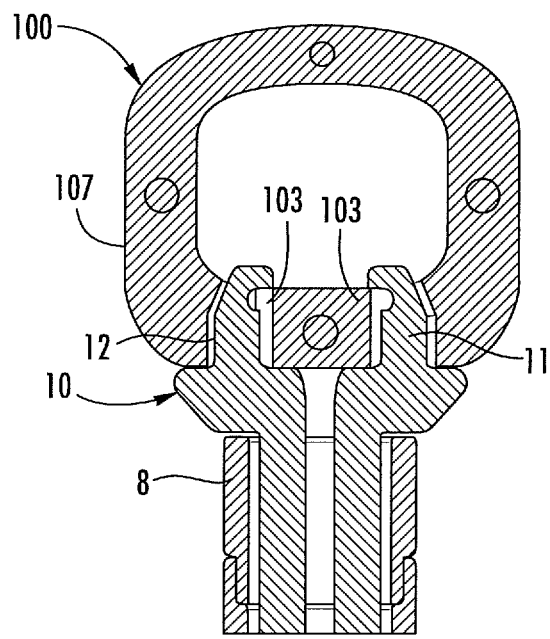
FIGS. 9 and 10 are side views of the instrument distal portion in two different operative conditions, respectively, according to the present invention.
Figure 10:
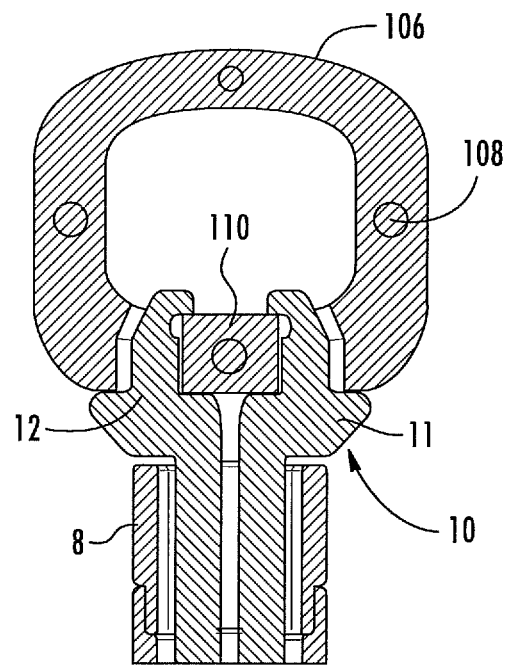

FIGS. 9 and 10 show the grasping head 10 of the positioning instrument 1 in two different operating positions, respectively. The first position corresponds to the insertion of the prongs 11, 12 into the holes 103 of the body implant 102 of the implant 100 and the second position corresponds to gripping of the portion 110 of the proximal major side 105 with the prongs 11, 12 coming close one to the other, reducing the thickness of the cut 18.

The rotational movement to lock the grasping head 10 can be between 10° and 130° degrees. A 90° degree movement is a preferred locking option; however, the instrument structure may allow a free relative rotation between the shaft 7 and the stem 15 between 0° and 130° with continuity.

It should be noted that all essential parts of the instrument 1 can be disassembled for cleaning and sterilization.

The instrument locking function is operated with the help of the thumb wheel 9, which is part of and fixed to the locking shaft 7. By turning the thumb wheel for +/−90° a relative movement of the stem 15 distal portions 11, 12 or 31, 32 is obtained inside the cannulated shaft 7.

The core element of the instrument 1 is the stem 15, which can be axially secured inside the handle 3 with the help of the fastener nut 19 screwed on the threaded portion 17 of the stem proximal end. The shaft 7 is free to rotate outside the stem 15.

The Locking shaft 7 is axially secured on the instrument 1 with the help of a fast bayonet coupling 23 that stops a possible axial movement with respect to the distal end 5 of the sleeve 4. In addition the second groove 26 of the bayonet coupling 29/23 also defines/limits the amount of the allowed axial rotation. The grasping head 10 of the stem 15 in its rest position is normally presenting the prongs 11, 12 at a predetermined distance one from the other to offer an open position of the instrument 1 ready to grip the engagement portion 110 of the implant 100.

The shaft 7 can be turned or rotated with respect to the stem 15 covering with continuity and with an angular extension of +/−10°-130° with a preference for a 90° range. The oval section of the collar 8 of the cannulated shaft 7 allows performing an equal turning movement. This rotation results in a closing movement of the two prongs 11, 12 of the grasping head 10 that approaches one close to the other, gripping the engagement portion 110 of the implant 1, as shown in FIGS. 9 and 10.

Figure 27:
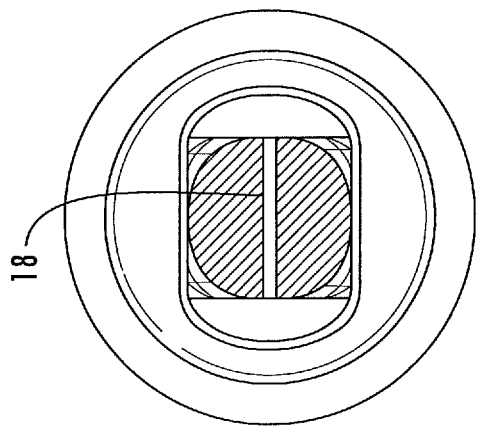
FIGS. 25, 26 and 27 are cross-sectional views of the instrument distal portion taken along the line F-F of FIG. 20 in different operative conditions, respectively.
Figure 26:
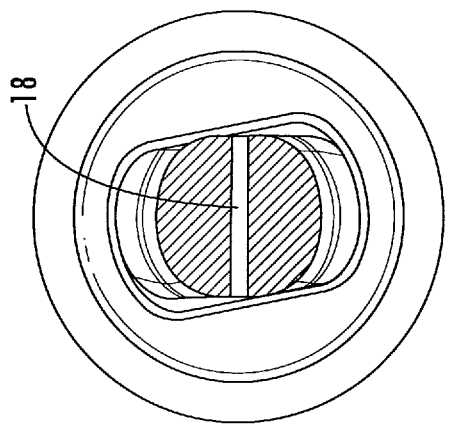

The internal oval section of the collar 8 of the locking shaft 7 forces the two distal portions of the stem 15, forming the grabbing head 10, and separated by the cut 18, into a locking position as shown in the FIG. 10. Some of the possible different relative positions of the stem 15 with respect to the collar 8 of the cannulated locking shaft 7 are shown in FIGS. 25 to 27.

Figure 25:
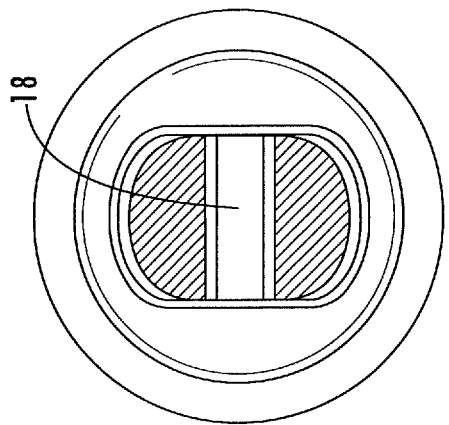

In FIG. 25, the cut 18 shows that the two prongs 11, 12 or clamps 31, 32 are in the rest position far from each other. In FIGS. 26 and 27, the air gap in the cut 18 is reduced since two end portions of the stem 15 are closer to one another in view of the rotation of the stem in one or in the other +/−90° angular position.

This possibility of reducing the air gap of the cut 18 is used to force the prongs 11, 12 or the clamps 31, 32 to get closer, grasping the engagement portion 110 of the implant 100. When locking the instrument application of the prongs 11, 12 grasp the portion 110 securely and allow axial force (push or pull) and some torque to manipulate and correctly position the implant in situ.

As a whole, the locking action is performed by a rotational movement having an angular range between 10° to 130°, either of the locking shaft 7 or of the stem 15 with respect to the handle. The instrument 1 of the present invention may be used to install implants having different structure than that previously disclosed with the reference number 100.

Figure 11:
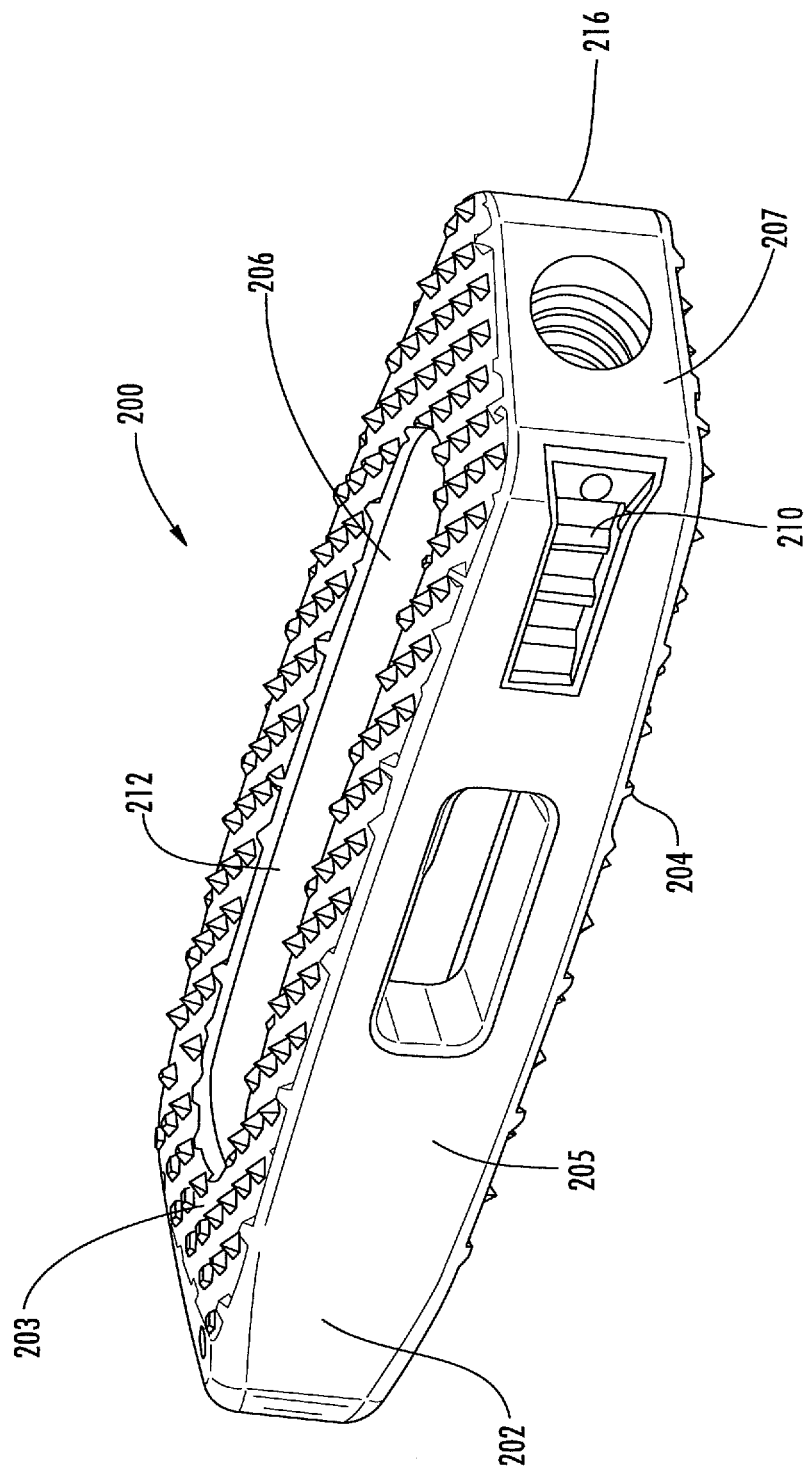
FIG. 11 is a perspective view of an implant for the fusion between two vertebral bodies of a spine positioned by an alternative embodiment of the instrument of FIG. 2.

For instance, in FIG. 11, another example is shown of an implant 200 having a different structure. The implant 200 still has been specifically realized for allowing vertebral operations according to the requirement of the modern Minimal Invasive Surgery. The implant 200 has a main body 202 realized with a biocompatible radiolucent synthetic material, for example, a Polyetheretherketone (PEEK) structure having a favorable modulus of elasticity.

The body 202 has a substantially elongated rectangular shape with rounded edges and is available in several different heights, widths, and lengths. This rectangular shape has two opposite major sides 205, 206 and two opposite minor sides 207.

The body 202 has two opposite surfaces 203 and 204 coming into direct contact with the vertebral column to fit the anatomy of the vertebral end plates. The body 202 includes cavities 212 for filling purposes allowing the bone growth (e.g. autogenic bone graft).

The implant 200 has symmetrical angular openings 210, 211 provided at the corner between the two major sides 205, 206 and a same minor side 207.

As clearly shown in FIG. 12, the instrument 50, provided with clamps 31, 32 is suitable for grasping and positioning the implant 200 by the action of the grasping head 10, clamping the two openings 210, 211 of the implant 200.

The clamps 31, 32 have internal teeth 41 for better gripping action. Even if it is not detailed by other drawings, the internal structure of the instrument with the clamps 31, 32 is identical to the structure already disclosed with reference to the FIG. from 5 to 13. The instrument of the present invention needs much less space for in-situ manipulation than the prior art handling and locking mechanisms, and the space is critical due to the fact that it drives the size of the surgical incision. This function enables minimally invasive implantation as the implant can be inserted in the direction of the smallest cross section and the turned in situ into the correct position.

The mechanical structure of the instruments 1 or 50 of the present invention may be used to realize slightly different alternative embodiment like the one shown in the Figures from 15 to 24 with the numeral 70.

Figure 14:
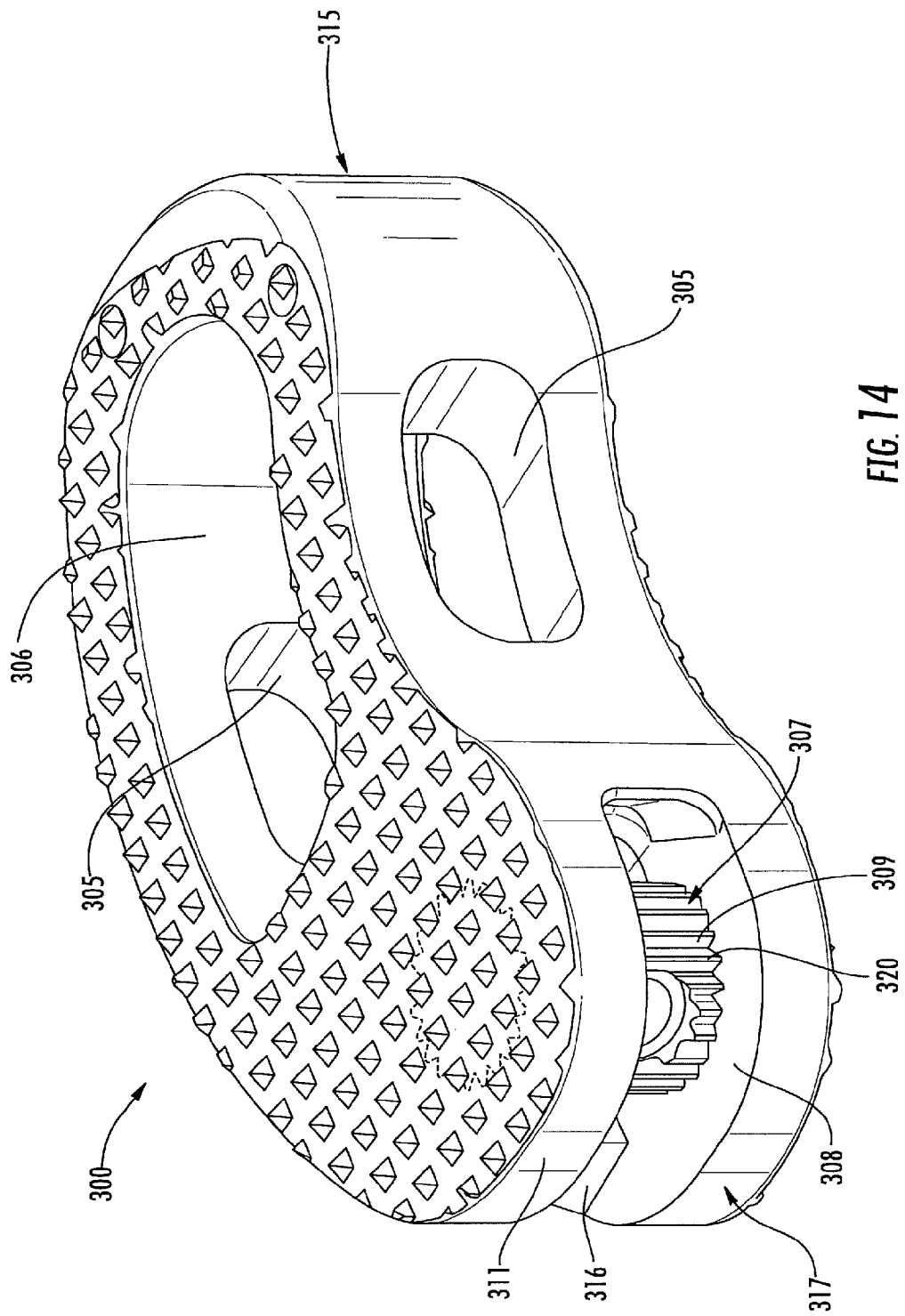
FIG. 14 is a perspective view of an implant for the fusion between two lumbar vertebral bodies of a spine positioned by another embodiment of the instrument, according to the present invention.
Figure 15:
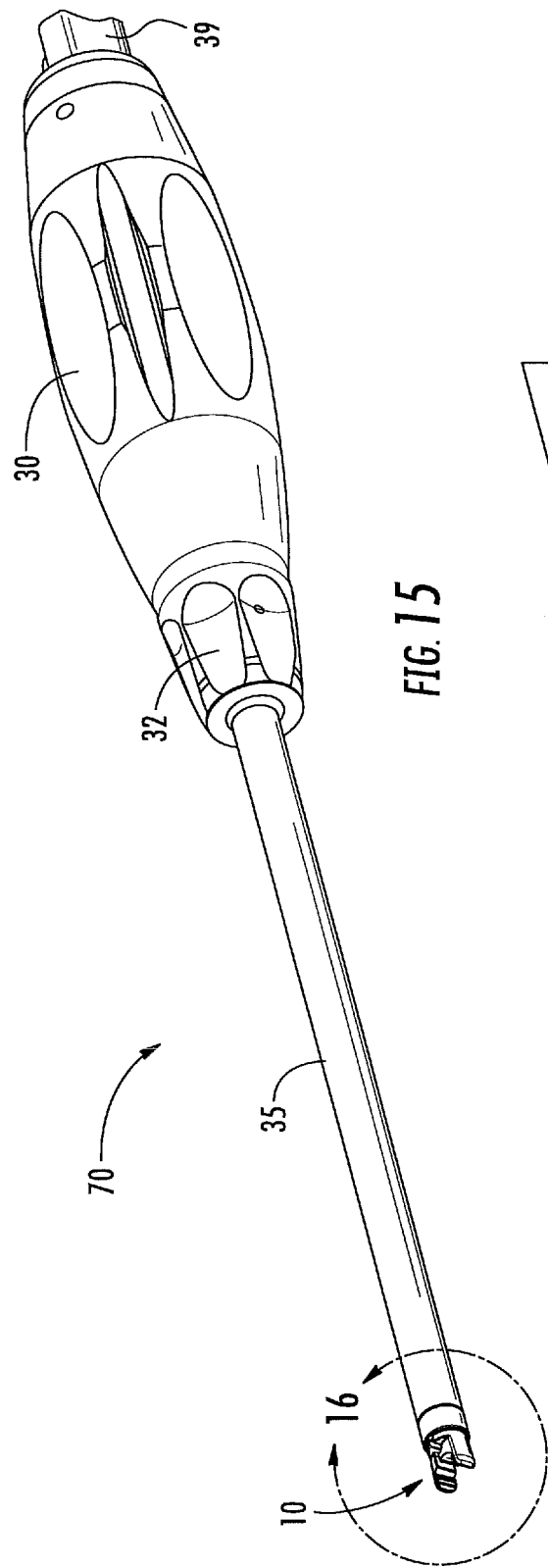
FIG. 15 is a perspective view of an instrument for positioning the implant of FIG. 14, according to the present invention.
Figure 16:
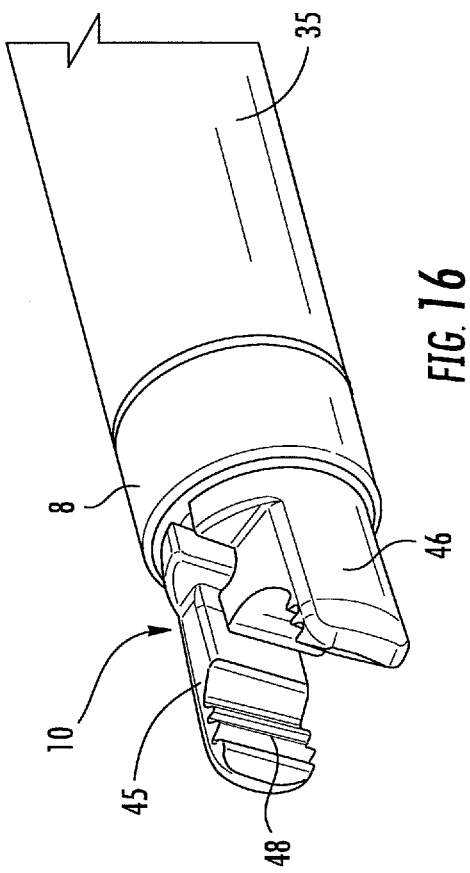
FIG. 16 is an enlarged perspective view of a part of the instrument of FIG. 15.
Figure 17:
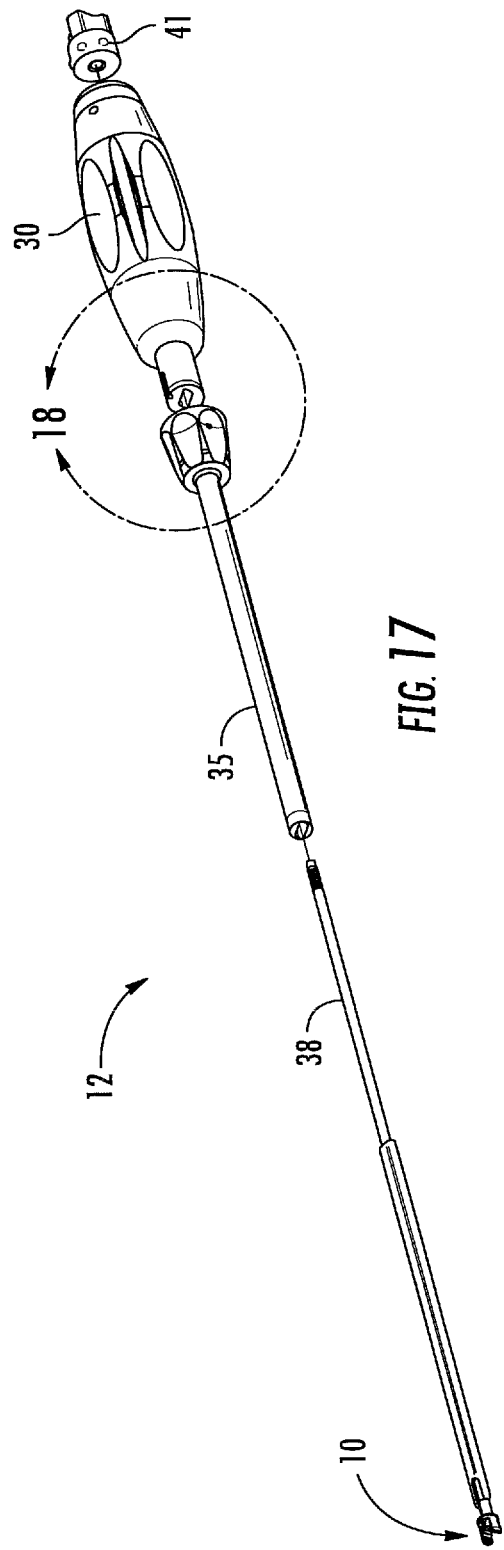
FIG. 17 is a perspective view of separate parts of the instrument of FIGS. 15 and 16.
Figure 18:
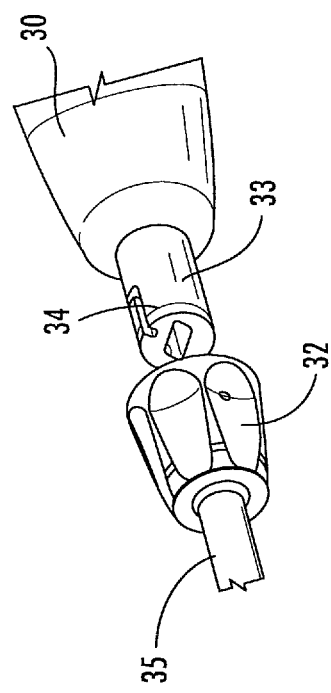
FIG. 18 is an enlarged perspective view of a part of the instrument of FIG. 17.
Figure 21:
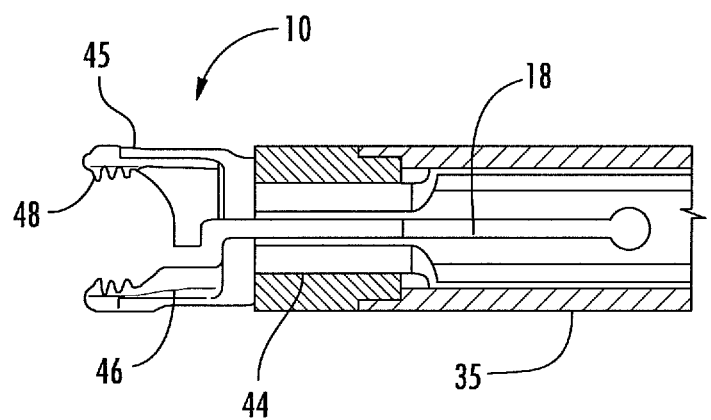
FIG. 21 is an enlarged cross-sectional view of FIG. 20 and in particular of the instrument distal portion.
Figure 22:
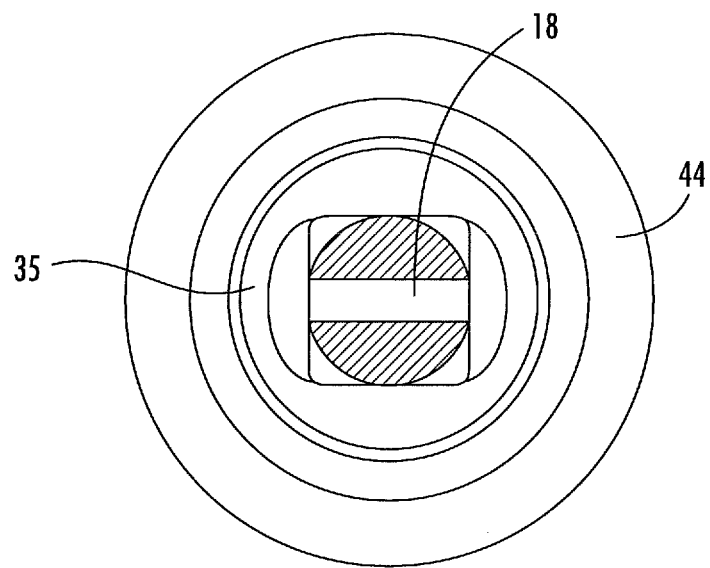
FIG. 22 is a cross-sectional view of the instrument distal portion taken along the line F-F of FIG. 20.

This instrument is used to install an implant 300 having a different structure than the implants 100 and 200 previously disclosed with the reference to the FIGS. 1 and 14. The structure of this implant 300 is first disclosed and, the structure and functioning of the alternative instrument 70 is disclosed thereafter.

The implant 300 is mainly dedicated to the use in TLIF (Transforaminal Lombar Intervertebral Fusion) surgery; however, nothing prevents its use in other surgery techniques, such as PLIF or OILF.

The implant 300 has a main body 302 realized with a biocompatible radiolucent synthetic material, for example, a Polyetheretherketone (PEEK) structure having a favorable modulus of elasticity.

The body 2 is Kidney-bead shaped and available in several different heights, widths, and lengths. Moreover, some markers 311 are incorporated in the biocompatible synthetic material of the implant body 302. The body 302 includes holes 305 or cavities 306 for filling purposes, allowing the bone growth (e.g. autogenic bone graft). The body 302 has one end 315 named insertion nose and the opposite end 317 provided with an engagement portion 307. Advantageously, the engagement portion 307 is provided for receiving the grasping end 10 of the positioning instrument 70.

The engagement portion 307 is a splined shaft 309, similar to a gear and that is accessible through a lateral opening 308 of the body 302. Advantageously, the splined shaft 309 has a substantially cylindrical shape, presenting a plurality of ribs 320 along its peripheral surface. Those ribs 20 are regularly angularly spaced as in a gear and provided in a number varying from ten to eighty.

More particularly, the splined shaft 309 has a plurality of ribs 320 regularly alternated by groves with a regular and relatively small pitch, thus forming the gear shape of the shaft. This particular shape allows the engagement portion 317 to be strongly clamped by the gripping end of the instrument 70, and this clamping action may be performed in different positions, as shown hereinafter.

The splined shaft 309 offers a positive lock between the grabbing head 10 of the instrument 70 and the implant 300. The opening 308 is delimited by at least a lateral wall 316 that represents a lateral stop for the possible angular orientation of the grasping head 10 of the instrument 70 when such a grabbing head 10 is engaging the splined shaft 309. This mechanical stop 316 also gives a feedback of the position of the implant 1 in relation to the positioning or insertion instrument 70.

The body 302 of the implant 300 may be manufactured by PEEK while the splined shaft 309 may be manufactured by a suitable biocompatible alloy, for example, Titanium or a Titanium alloy. The implant 300 has the advantage that may be easily and firmly handled by the instrument 70 for inserting or removing the implant into and out from an intervertebral space between adjacent vertebral bones.

Due to the stable lock between the instrument and the implant, a perfect controlled angular adjustability of the implant in-situ is possible. The present invention also relates to the instrument 70 structured for positioning an intervertebral implant like the implant 300 in the spinal column.

The instrument 70 allows simple manipulation of an implant like the implant 300 by the instrument grasping head and with a quick 90° oval locking feature. The connection is allowed by way of ribs and grooves of the splined shaft 309 in the implant 300 and the corresponding teeth of clamps 45, 46 forming the grasping head 10 that allows the fixation at one predefined position or the fixation in multiple predefined positions to the instrument. Different grasping mechanisms are described in the prior art, but those instruments need several turns to fix the implant to the instrument or a significant linear movement on the instrument or a complex hinge mechanism.

A simple 90° rotation of the instrument thumb wheel 9 provides a locking mechanism that significantly simplifies the engagement and disengagement of the implant 1 or of a similar implant structure, as shown hereinafter.

In addition, known instruments with a significant axial displacement can cause tissue damage. Pliers like instruments usually have an excessive space requirement which is in such applications critical because it requires larger incisions and can usually not be used in Minimally Invasive surgeries. The positioning instrument 70 for the TLIF implant comprises various components.

A handle 30 allows secure holding of the instrument 70. Inside the handle, an elongated sleeve 31 is hosted. The distal end 33 of this sleeve 31 is connected to a locking shaft 35 that is extended along an X axis aligned with the same axis of the handle 30. The locking shaft 35 terminates with a distal end portion including the grasping head 10.

A collar 44 is mounted on the distal end of the locking shaft 35 while the grabbing head 10 extends outside the collar 44. The locking shaft 35 is longer than the handle 30 and the connection between the shaft 35 and the distal end of the sleeve 31 is protected by a thumb wheel 32. The connection between the shaft 35 and the distal end 33 of the sleeve 31 may be obtained in different manner, but a bayonet coupling 34 is preferred in this embodiment, as shown in FIG. 14.

The locking shaft 35 is cannulated and a stem 38 is inserted inside the shaft 35 and the sleeve 31 up to the proximal end of the handle 30. The longitudinal hole forming the cannulated passage has an oval section in its distal end, as can be appreciated from the perspective view of FIG. 12, showing also the oval section of the sleeve passage, as well as from the cross section of FIG. 10, showing the internal oval section of the locking shaft 35 close to its distal end. As an alternative, the cannulated passage may have a rectangular section with rounded edges. The stem 38 has a main cylindrical cross section.

The proximal end of this stem 38 is provided with a threaded portion 37 to allow the fastening of a terminal fastener nut 39, shown in FIG. 6. The nut 39 prevents the instrument from being disassembled when in use.

The stem 38 and the handle 30 have a partially rectangular cross-section at their interface at the distal end of the handle. This means that the stem 38 can't rotate with respect to the handle 30. In this embodiment, it is only possible to rotate the locking shaft 35 with respect to the stem 38 and the handle 30 through the thumb wheel 32. However, it's possible to rotate the stem during the assembly phase in order to find the rectangular counterpart in the handle 30.

A skilled person in the art will appreciate that an alternative structure may be provided with the locking shaft fixed to the handle and the stem being free to rotate with respect to the locking shaft to cause the locking function. However, in the embodiment here disclosed, the cannulated shaft 35 is rotatable on the stem 38. A ball positioner 43 prevents the fastener nut 39 from falling out of the handle 30.

With reference to the examples of FIGS. 19 to 22, it will be disclosed the structure of the distal end portion of the instrument 70. The grasping head 10 is the distal terminal portion of the stem 38 and is formed by a couple of faced clamps 45, 46. Both clamps present an internally curved surface having a teethed portion 48 with ribs and grooves substantially corresponding in shape to the ribs 20 and grooves 21 of the splined shaft 309.

Figure 23:
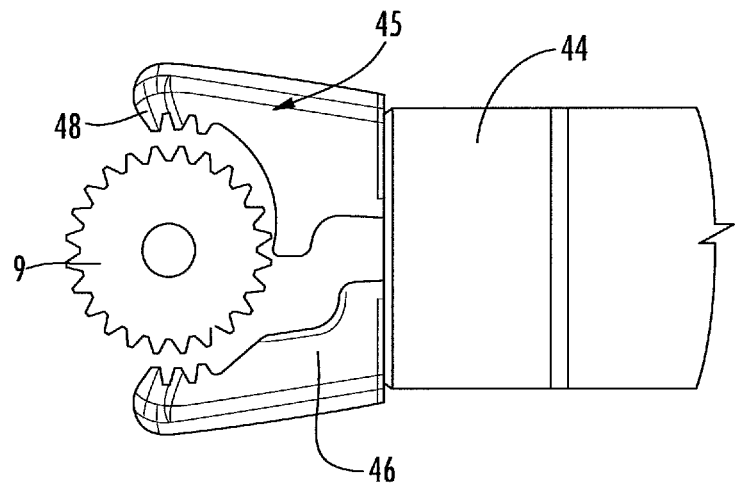
FIGS. 23 and 24 are side views of the instrument, according to the present invention, distal portion in two different operative conditions, respectively.
Figure 24:
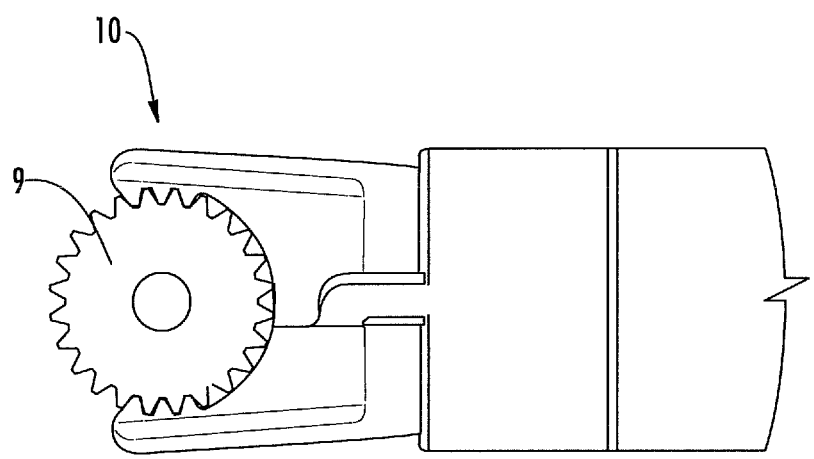

A cut 18 is provided at the distal end of the stem 38 for a short extension, thus separating the two clamps 45, 46 and allowing a reciprocal elastic movement between them. The cut 18 is extended more than the extension of the stem oval section. FIGS. 23 and 24 show the grasping head 10 of the positioning instrument 70 in two different operating position, the first approaching the splined shaft 309 of the implant 300 and the second grasping such a splined shaft 309 with the clamps 45, 46 closed on the gear shape of the splined shaft 309. The different relative positions of the stem 38 inside the cannulated locking shaft 35 having internal oval section are shown in the FIGS. 25, 26 and 27.

In FIG. 25, the cut 18 shows that the two clamps 45, 46 are in the rest position far one from one another. In FIGS. 26 and 27, the air gap in the cut 18 is reduced since two end portion of the stem 38 are closer one to the other in view of the rotation of the shaft 35 in one or in the other +/−90° angular position. However, just a reduced angular movement of only 10° may start the approaching movement of the two end portion of the stem forming the clamps 45, 46. It should be noted that all essential parts of the instrument 70 can be disassembled for cleaning and sterilization.

The instrument locking function is operated with the help of the thamb wheel 32, which is part of the locking shaft 35. By turning the thumb wheel for +/−90°, a relative movement with respect to the stem 38 is obtained rotating the cannulated shaft 35. An angular range between 10° and 130° may allow a gripping action of the two clamps 45, 46.

The core element of the instrument 70 is the stem 38, which can be secured inside the handle 30 with the help of the fastener nut 39 screwed on the threaded portion 37 of the stem proximal end but it is supporting the rotatable shaft 35. The locking shaft 35 is secured along the axial direction on the instrument 70 with the help of a fast bayonet coupling 33 already disclosed in detail with respect to the previous embodiments.

The grasping head 10 of the stem 38 in its rest position is normally pre-deformed in order to offer an open position of the instrument 70 ready to grip the splined shaft 309 of the implant 300. The two clamps 45, 46 have a slightly different structure and are not symmetrical to avoid the presence of a groove aligned with the cut 18.

The shaft 35 can be turned or rotated over the stem 38 covering +/−130°, with preference for 90°, and the oval section of the cannulated shaft 35 allows an equal turning movement. This rotation results in a closing movement of the two clamps 45, 46 of the grasping head 10 approaches one close to the other, grasping the splined shaft 309 of the implant 300, as shown in FIGS. 23 and 24.

The internal oval section of the locking shaft 35 forces the two distal portions of the stem 38 forming the grabbing head 10, and separated by the cut 18, into a locking position, as shown in the FIG. 24. This function is used to grab or release the splined shaft 309 of the implant 300 and allows holding/manipulating the implant at several angles. When locking the instrument, the ribs 320 are engaged and allow the transmission of torque in order to manipulate and correctly positioning the implant in situ.

When an angle between the implant and the instrument of at least of 60° is reached, the mechanical stop 316 avoids further increase of the angle as it is in contact with the stopping surface of the instrument clamps 45 or 46. This gives a feedback of the position of the implant relative to the instrument.

That which is claimed is:

1. An instrument for positioning an intervertebral implant for the fusion between two vertebral bodies of a vertebral column, comprising:
   a handle having a proximal end and a distal end;
   a locking shaft extended from the distal end of the handle;
   a grasping head at the distal end of the instrument;
   said locking shaft is cannulated and a stem is hosted inside the cannulated shaft and fixed to the handle;
   said locking shaft is free to rotate with respect to the stem;
   said grasping head being formed at the distal end of said stem with a couple of prongs coming close or far one toward the other according to an angular relative rotation of said locking shaft with respect to the stem;
   wherein said cannulated locking shaft has a distal collar having an internal oval section interfering with the stem during relative angular rotation.

2. The instrument according to claim 1, wherein a cut is provided at the distal end of the stem along its axis separating the two prongs or clamps and allowing a reciprocal elastic movement between them.

3. The instrument according to claim 2, wherein said cut is extended more than the extension of the stem oval section of the collar.

4. The instrument according to claim 1, wherein a sleeve is incorporated inside said handle with a distal end projection from said handle; said shaft being rotatable mounted on said distal end of the sleeve through a thumb wheel.

5. The instrument according to claim 4, wherein said stem is extended through said sleeve up to the proximal end of the handle and has a threaded end to be fixed by a nut at the proximal end of the handle.

6. The instrument according to claim 1, wherein said clamps include internal teeth for improving the gripping action.

7. The instrument according to claim 1, wherein said stem is rotatable with respect to a locking shaft fixed to the handle.

8. The instrument according to claim 1, wherein the locking action is performed by degree rotational movement between 10° and 130°, either of the locking shaft or of the stem with respect to the handle.

9. The instrument according to claim 1, wherein the locking action is performed by a rotational movement having an angular range of 90° either of the locking shaft or of the stem with respect to the handle.

10. The instrument according to claim 1, wherein said clamps have an asymmetrical structure.

11. The instrument according to claim 1, wherein said clamps include an internally curved surface having a teethed portion.

* * * * *